United States Patent [19]

Seiner

[11] 4,035,085

[45] July 12, 1977

[54] METHOD AND APPARATUS FOR COMPARING LIGHT REFLECTANCE OF A SAMPLE AGAINST A STANDARD

[75] Inventor: Jerome A. Seiner, Pittsburgh, Pa.

[73] Assignee: PPG Industries, Inc., Pittsburgh, Pa.

[21] Appl. No.: 638,213

[22] Filed: Dec. 5, 1975

Related U.S. Application Data

[62] Division of Ser. No. 375,198, June 29, 1973, Pat. No. 3,956,201, which is a division of Ser. No. 741,502, July 1, 1968, Pat. No. 3,764,364.

[51] Int. Cl.² ............... G01J 3/46; G01N 21/48
[52] U.S. Cl. .................. 356/179; 356/195; 356/212; 356/243
[58] Field of Search .......... 356/173, 179, 191, 194, 356/195, 209, 210, 212, 243

[56] References Cited

U.S. PATENT DOCUMENTS 3,504,963   4/1970   Davies et al. ............... 356/243 X
3,512,895   5/1970   Grum et al. ................. 356/243

Primary Examiner—Edward S. Bauer
Assistant Examiner—F. L. Evans

[57] ABSTRACT

Fluorinated aliphatic long chain addition polymers comprised of at least one monomer having at least one fluorine atom attached to a chain carbon atom are used in various environments for their ability to reflect a high percentage of incident light having a wave length in the 2400 to 8000 Angstrom region. These reflectance polymers may be in pressed powder form or in film form and thus are especially applicable as reflectance standards and reflectance coatings particularly in light integrating spheres of spectrophotometers.

10 Claims, 2 Drawing Figures

METHOD AND APPARATUS FOR COMPARING LIGHT REFLECTANCE OF A SAMPLE AGAINST A STANDARD

This is a division, of application Ser. No. 375,198, filed June 29, 1973, now U.S. Pat. No. 3,956,201 is a division of application Ser. No. 741,502, filed July 1, 1968, now U.S. Pat. No. 3,764,364.

BACKGROUND OF THE INVENTION

This invention relates to standards and coatings. More specifically this invention relates to the use of fluorinated polymers as general reflectance standards and coatings.

For many years industries which must measure, test or otherwise use light reflectance have been faced with the problem of having to use materials for general reflectance or reflectance standard purposes (i.e. either white or colored light) which are either unstable to light and thus age poorly or which reflect a low percentage of incident light and thereby fail to meet the degree of quality necessary to effect good reflectance. This problem is especially acute in those industries where these materials must be used either as reflectance standards or as reflective coatings in light integrating spheres used in various measuring and testing devices such as spectrophotometers, colorimeters, and spectrofluorometers. Devices of this nature are well known in the art and are best exemplified by the Pineo Spectrophotometer (U.S. Pat. No. 2,107,836), the Taylor Absolute Reflectance Instrument (Scientific Papers of the Bureau of Standards, Vol 17, pp. 1-6, 1922), the General Electric Spectrophotometer, the IDL "Color Eye," and the Beckman "DU."

Examples of materials currently used for reflectance coatings and standards which give rise to the above problem include pigmented paint, smoked magnesium oxide, magnesium carbonate, and barium sulfate. Pigmented paint, for instance, may be of low reflectance, give rise to light stability problems, and may crack and chip upon aging. Magnesium oxide and magnesium carbonate have been used for many years but their reflectance characteristics and physical properties present problems of light stability and reflectance inefficiency. Barium sulfate, presently the most commonly used white light reflectance standard and sphere coating material, can be made to reflect essentially 100 percent of incident light having a wave length from 2400 to 8000A and thus forms an almost ideal white standard. However, this compound is easily degraded to only about 90 percent of this value after a few days of use. Degradation of this compound is especially rapid when light having wave lengths from 2400 to 4000 A are used, thus seriously affecting the ability to use this compound in devices for measuring, testing or otherwise dealing with ultraviolet light.

From the above discussion it is clearly seen that a long-felt need has existed for a highly reflective material which is also light stable.

SUMMARY OF THE INVENTION

This invention provides a material which may be used for white light or color reflectance purposes and which is light stable and yet has a high degree of reflectivity. The material of this invention may be used in various forms so as to be useful as a coating or as a reflectance standard.

According to one aspect of this invention there is provided a film, alone or coated on a substrate, which includes at least one fluorinated aliphatic long chain addition polymer comprised of at least one monomer having at least one fluorine atom attached to a chain carbon atom, said film being of a sufficient thickness to reflect more than 90 percent of incident light having a wave length of from 2400 to 8000 Angstrom units.

According to another aspect of this invention there is provided a film, alone or coated on a substrate, comprised of the above-described polymer and having therein a plurality of discrete cells, said film being of a sufficient thickness to reflect more than 90 percent of incident light having a wave length of from 2400 to 8000 Angstrom units.

According to still another aspect of this invention there is provided a film comprised of the above-described polymer which has dispersed therein a coloring material. Such a film may then be advantageously used as a color standard for the color of the pigment since the film reflects more than 90% of incident light having wave lengths at which the pigment is transparent, said wavelengths being between 2400 and 8000 Angstrom units.

The concept of light reflectance is well known in the art and the terms "reflectance" and "reflect . . . incident light" are used herein to describe this well known concept. That is to say, these terms are used to define that characteristic of a body which enables it to throw back or return incident light rather than to absorb it.

The term "90 percent of incident light having a wave length of from 2400 to 8000 Angstrom units" is used herein to describe what the art considers a useful level of white light reflectivity or "whiteness" of a body. That is to say in order for a body to truly be "white" enough for white light reflectance standard purposes it must not absorb more than 10 percent of incident light having wave lengths in the above ranges. Actual commercial values, of course, approach zero percent absorption or ideal whiteness as was seen in the case of $BaSO_4$ hereinbefore set out. But as already stated, $BaSO_4$ rapidly deteriorates in this light (2400 to 8000 A) and especially in light having wave lenghts of from 2400 to 4000 A (ultraviolet light).

DETAILED DESCRIPTION OF THE INVENTION

Figure 1:
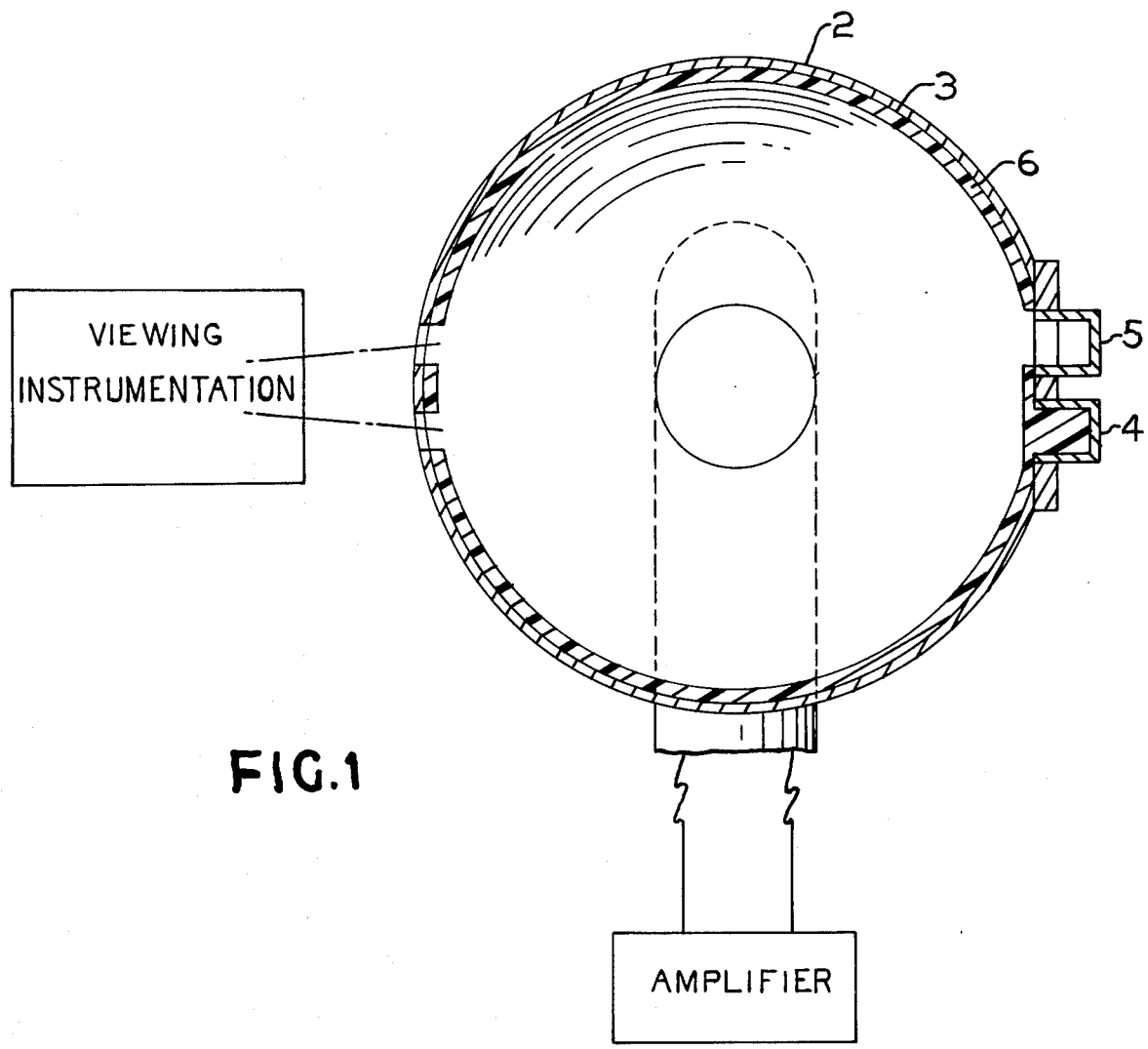
FIG. 1 is a sectional view of a light integrating sphere adapted for use in a Pineo type spectrophotometer and exhibiting therein both a coating and a reflectance standard made from the material of this invention.

The class of materials contemplated for use in this invention is defined by those materials which comprise at least one fluorinated aliphatic long chain addition polymer comprised of at least one monomer having at least one fluorine atom attached to a chain carbon atom.

Polymers which fall within the above described class of materials are well known in the art and include the various homopolymers of the above described monomers, copolymers of these monomers and other monomers not of the above described class, and crosslinked polymers formed from these homopolymers and copolymers which will conform to the hereinafter described reflectance requirements. Some examples of these polymers are; polytetrafluoroethylene, polychlorotrifluoroethylene, polychlorofluoroethylene, polyvinylidene fluoride, and polyvinyl fluoride.

Some examples of monomers which may be used to make up both hompolymers and copolymers of the above-described polymers within the aforementioned class of materials are: 1,3-butadiene hexafluoride, 1-chloro-1-fluoroethylene, chlorotrifluoroethylene, 1,1-difluoroethylene, vinyl fluoride, 1-fluoroacrylonitrile, and fluorinated acrylic acids such as 1-fluoroacrylic acid and 2,2-difluoroacrylic acid, and tetrafluoroethylene.

Examples of other monomers which may be used with the above described monomers to form copolymers within the aforementioned class of materials are: ethylene, propylene, acrylic acid, methacrylate esters and the like.

Methods of making these monomers and polymerizing them into the various polymers are well known. Thus, for the purposes of this invention, the polymers herein used may be made by any conventional polymerization process. For example, polyvinylidene fluorides may be made according to the procedure set forth in U.S. Pat. No. 2,435,537. Basically, this procedure comprises heating a vinylidene fluoride monomer either by itself or with promoters at temperatures ranging from 20° to 250°C. under a pressure above 3000 atmospheres in the presence of a peroxy polymerization catalyst until the polymer is formed. Another example, polytrifluoroethylene monomer along with 0.55% acetyl peroxide in a 6 inch steel bomb at temperatures ranging between −16°C. and 60°C. at sufficient pressures and for a sufficient period of time to obtain the polymer.

The materials of this invention which include the above described polymers may assume many forms and be placed in a variety of environments in which their high reflectance properties are needed.

For example, in one form, the material is a pressed powder reflectance standard. That is to say, a polymer of the type hereinbefore set out is pulverized to form a powder. This powder with or without adhesives is then subjected according to conventional methods to a pressing operations at sufficient pressures temperatures to form the powder into a cake or wafer of a shape suitable for mounting in a reflectance device as a reflectance standard. It is pointed out, however, that the pressure and temperature is applied only long enough to provide a cake which is opaque and which is of sufficient thickness to reflect more than 90 percent of incident light having a wave length of from 2400 to 8000 Angstrom units. Further pressure and high temperatures tend to make the cake less opaque and less reflective. Once formed, this cake or wafer may be suitably mounted in a sample holder and used as a reflectance standard in the various devices hereinabove mentioned.

Another form which this material may take is a film used as a reflectance standard. That is to say, a film is formed of the polymer wherein the film is provided with a plurality of discrete cells which when coupled with a sufficient film thickness and appropriate shape may be mounted on a sample holder and used as a reflectance standard in a reflectance device.

One very desirable way of making this film is by a solvent precipitation process as disclosed in application's copending application, Ser. No. 524,953, filed Feb. 1, 1966 now abandoned, the disclosure of which is incorporated herein by reference. This process as applied to this invention comprises dissolving one or more of the mentioned polymers in a solvent mixture which has at least two miscible liquids, at least one of the liquids being a non-solvent for the polymers and having a lower volatility than that of the other liquids in the mixture, until the polymers and solvent mixture form a single phase. The amount of lower volatility non-solvent used is less than that at which, upon removal of the solvent mixture from the composition produces a discontinuous film, but is at least sufficient to provide enough cells that together with the thickness of the film enables the formed film to reflect more than 90 percent of incident light having a wave length of from 2400 to 8000 Angstrom units and thereby form a truly white body. This solution is applied to a suitable surface by spraying or other means and the solvent mixture is allowed to evaporate. The evaporation may be natural or forced (as by baking). During evaporation, the more highly volatile liquid of the solvent mixture evaporates off first, causing the polymer to gel. With further evaporation, the gelled polymer forms into a film having entrapped therein a plurality of tiny droplets of the less volatile non-solvent. The final stages of evaporation cause this less volatile non-solvent to evaporate off through the polymer matrix, leaving microscopic voids in the rigid, white, non-pigmented film. The film is then mounted as a reflectance standard in the desired reflectance device either while still on the surface itself or after having been removed therefrom.

As alluded to hereinabove, the amount of non-solvent used may be varied so as to yield various cell characteristics in the final film. However, for purposes of this invention, the non-solvent is usually present in an amount which will form closed or open cells. In a preferred form, and upon the removal of the solvent mixture, the film will have a Kubelka-Munk scattering coefficient greater than 0.5 reciprocal mils at 4400 Angstroms and greater than 0.1 reciprocal mils at 5600 Angstroms. Such a coefficient range indicates efficient white opacity.

The Kubelka-Munk analysis is well known to the art and is discussed by D. B. Judd in "Color in Business, Science and Industry," John Wiley and Sons, New York, 1952 pp. 314–338, the disclosure of which is incorporated herein by reference.

In some instances it is desirable to use more than one polymer. Such an adaptation is well within the purview of the above process, provided the mixture is a solvent to all the polymers and contains a low volatility liquid which is a non-solvent to at least part of the polymers.

Another very desirable way of making the films of this invention is by a marginal film form flow control techique. This technique as applied to this invention comprises controlling the flow characteristics of particles of a polymer of the type useful in this invention in a latex during water removal from the lates system after a latex, liquid polymer non-solvent mixture has first been formed and applied to a substrate. By this control, the final permeability, porosity, opacity, and reflectance characteristics (upon later removal) of the film formed upon water removal and evaporation may be chosen and varied. The particular control technique used depends upon the type of polymer latex chosen.

Generally, it may be stated that for the non-film forming polymers in the above-described group of polymers useful in this invention, the technique of adding good film formers, marginal film formers, and plasticizers thereto is used so as to render the non-film former composition capable of forming a film upon water removal. Similarly, when dealing with marginal film-forming polymers, good film formers and plasticizers may be used fo purposes of this invention. When using good film formers, flow inhibiting agents including marginal film formers and non-film formers may be added to effect a desired result. Temperature control during water removal from the latex system is a technique generally applicable to almost all latexes used regardless of their ability to form films at room temperature. That is to say, for purposes of this invention, the temperature of a latex system is varied about the polymer's Tg (glass transition) point to effect the desired characteristics of the final film. Generally speaking, when making reflectance films for testing instruments, temperature is held above the Tg point of the polymer to insure that a continuous film is formed.

The terms "good film former," "marginal film former" and "non-film former" are terms well understood in the art. The use of this technique in this invention enables many polymers to be used in film for their high reflectance characteristics which could not be formed into films adequate for purposes of reflectance standards and coatings. As was characteristic of the films formed by the solvent precipitation technique, this flow control technique, upon removal of the non-solvent entrapped in the formed film (e.g. by evaporation), forms films having threrein a plurality of discrete voids which render the film highly opaque and reflective.

The materials of this invention as hereinbefore described find particularly advantageous utility in the form of coatings. These coatings may be in powder of film form and may be used either as reflectance standards or for general reflectance purposes. For example, a powdered polymer mixture containing at least one fluorinated aliphatic long chain addition polymer comprised of at least one monomer having at least one fluorine atom attached to a chain carbon atom, may be coated upon a substrate by any conventional method until the coating is thich enough so that it reflects more than 90 percent of incident light having a wave length of from 2400 to 8000 Angstrom units.

One suitable way of forming this coating is to provide the substrate with an adhesive such as a wet lacquer or primer and then brush, spray of press the powder onto the lacquer of primer until the above characteristics are achieved. This brushing, spraying, or pressing may be done either in dry or inert liquid dispersion form and several applications may be required to achieve the desired results. It is understood, of course, that the polymer power need not be a mixture but may be a powder of a single polymer.

Another way in which this coating may be achieved is to form a film rather than a powder on the substrate. This film may be formed by the solvent precipitation process hereinbefore described, using the same techniques set forth therein except that the generally described "suitable surface" in that method is now replaced by an adhering substrate. The marginal film forming control technique as above-described may also be used to form a film coating in the same way that the solvent precipitation technique is used. As alluded to hereinabove, this flow control technique enables the porosity of the film to be varied. When using techniques other than this flow-control technique, the porosity of the film may be varied by admixing therewith, usually prior to forming the film, one or more transparent pigments, such as are silica, which do not absorb any appreciable amount of lighth of wave lengths from 2400 – 8000A.

The substrate contemplated for use herein upon which the unique class of materials of this invention may be placed may assume various shapes and forms suitable for adapting the high reflectance characteristics and light stable characteristics of the materials of this invention to a particular environment. For example, the excellent stablity characteristics of the films and powder coatings as above-described when reflecting ultra-violet light allows them to be used as paint coatings in sickrooms and poultry sheds for their antibactricidal effect arising out of their high reflection of incident ultraviolet light. Such coatings may also be used on the ground or elsewhere in vineyards, orchards etc. where increased reflection of ultraviolet light is beneficial to the crop being grown. In this respect, the coating on the ground or elsewhere is preferably applied by means of the above-described flow-control technique or by admixing transparent pigments (e.g. arc silica) therewith to insure sufficient porosity of the film in order to allow fertilizer, moisture, and air to penetrate the film and feed the crop. Other examples of substrates contemplated include inside walls of various building structures so as to brighten the rooms therein, outside walls of structures to thereby provide heat reflecting means for preventing the sun form raising the temperature of the innerstructure, and inside surroundings of electric light fixtures to provide better reflectance of light and therefore more efficient use of the light coming therefrom.

Although numerous other examples will become obvious to the skilled artisan once given the above teachings, an especially preferred form of substrate for the purposes of this invention is a substrate which when coated with the materials of this invention is mountable as a reflectance standard is a reflectance device such as a spectrophotometer and the like. In another preferred form the substrates are light integrating spheres of reflectance described and the coatings are located on the inner surfaces or walls thereof. The substrates are considered preferred since the materials of this invention, as discussed hereinabove, solve a long felt need in this environment. That is to say these materials may be used without the addition of opacifying pigments to reflect more than 90 percent of incident lightl having a wave length of from 2400 to 8000 Angstrom units. Thus, they are useful as coatings and standares in measuring and testing devices. These materials also reflect greater than 90 percent of incident light in the narrower critical ranges of 3800°–7000A° and 3200°–8000°A, the being the visible range and the latter being the range of fluorescence. Such reflectance characteristics allow the use of these materials not only in general spectrophotometers, but in spectrofluorometers (i.e. devices for evaluating fluorescent materials) as well.

Due to the versatility and durability of the abovedescribed high reflectance standards and coatings formed from the materials of this invention, it is also contemplated by this invention to admix a coloring material with these basic "white" standards and coatings and use the resulting materials as color standards and color coatings in various environments. The actual admixing of a coloring material with the basic materials of this invention may be accomplished by any conventional technique. In a preferred embodiment, however, the colored film is formed by the above described solvent precipitation technique. When forming a colored film by this solvent precipitation technique, a coloring material such as a pigment is preferably added when the polymer is dissolved is the solvent or more preferably it is first added to the non-solvent wherein after the polymer is prewetted with the non-solvent-pigment mixture and then dissolved in the solvent. After the solvent mixture is applied to a substrate and the solvent and non-solvent are evaporated therefrom to form a film having therein a plurality of discrete cells, it is found that within the film and/or cells therein there are present particles of pigment which color the film. That is to say, the film now absorbs light having wave lengths as characterized by the color of the pigment but still reflects more than 90 percent incident light in those wave length at which the pigment is essentially transparent.

Figure 2:
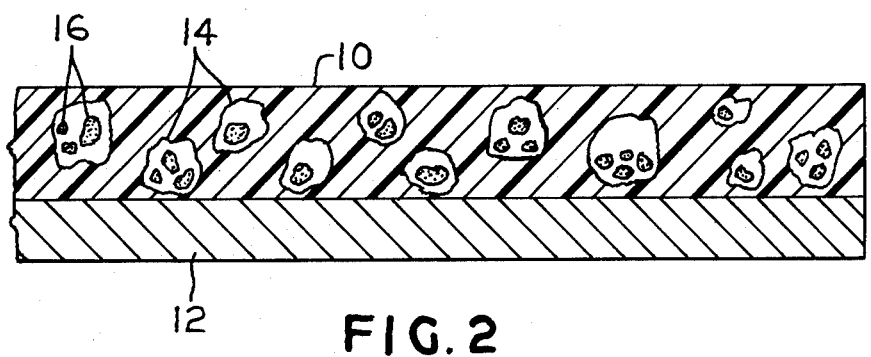
FIG. 2 is a sectional view of a substrate coated with a film formed of a polymer as contemplated by this invention. The film is provided with discrete cells having pigment particles therein and thus may be used as a color standard.

An example of a typical colored film formed by the solvent precipitation technique as adapted for purposes of this invention is illustrated in FIG. 2. In this FIG., a film 10 comprised of a polymer of the class as above described is coated upon a substrate 12. Within the film there is located a plurality of closed cells 14 having coloring pigment particles 16 therein. It is understood, of course, that this FIG. illustrates but a single embodiment of a colored film since many other embodiments are clearly contemplated by this invention. For example, some of the cells may be open rather than closed and/or the pigment may be dispersed in the polymer matrix 10.

The above-described high reflectance colored powdered coatings and films of this invention may be used in a wide variety of environments. One preferred enviroment, however, is a colorimeter wherein these powdered coatings and files may be used as color standards for the color absorbed by their incorporated pigment. As alluded to herebefore, their high reflectance and durability makes them particularly suitable for this purpose and thus solves a long-felt need in this art.

The following examples are illustrative of the above-described invention and are not meant as limitations thereon.

EXAMPLE 1

Powdered polyvinylidene fluoride is placed in a chromium plated compression sold 1.5 ;1 inches square. The powder (of approximately 5 microns particle size) is then subjected to a screw compression force sufficient to pack the powder at 25°C. The resulting article is a light stable, white, pressed powder cake of 1/8 inch thickness which raflects essentially 100% of incident light over the 2400 to 8000°A region when compared with barium sulfare that reflects at substantially the 100% level.

After two weeks of use, this block still retains essentially 100% of its original reflectance power over the full range as described above, while the pressed block of $Ba9O_4$, used for an identical length of time retains only about 90% of its original reflectance power over the SV part of this region. Referring to the FIG, there is depicted a light integrating sphere 2 of a spectrophotometer having a sample holder 5 and a standard holder 4. The cake of this example is mounted at 4 and used as a reflectance standard therein.

EXAMPLE 2

The same procedure is followed as in Example 1 except that polyvinyl fluoride powder is substituted for the polyvinylidene fluoride and the temperature (27°C.) is varied to meet the characteristics of this polymer. The cake produced has a thickness of ¼inch, is light stable, and has a reflectance of over 90% when used with light in the 2400 to 8000 Angstrom region.

EXAMPLE 3

The same procedure is followed as in Example 1 except that polychlorofluoroethylene powder is substituted for the polyvinylidene fluoride and the temperature (26°C.) is varied to meet the characteristics of this polymer. The resulting cake is light stable and has a reflectance of over 90% with light in the ranges heretofore set out.

EXAMPLE 4

The same procedure as in the above examples is followed using powdered polytrifluorochloroethylene with suitable adjustment of the variables. A cake having similar properties as set forth above is the result.

EXAMPLE 5

The same procedure as in the above example is followed using a 50—50 by weight mixture of polyvinylidene fluoride powder and polyvinyl fluoride powder. A cake having excellent light stability and reflecting greater than 90% of incident light in the above mentioned ranges results. This cake is then mounted as a reflectance standard 4 in a Pineo type spectrophotometer as shown in FIG. 1.

EXAMPLE 6

Fifty grams of polyvinylidene fluoride (tradename: "Kynar 500") are dissolved in 550 grams of hot acetone (100°F.). To this solution is slowly added 50 grams of Isopar H (an aliphatic hydrocarbon fraction polymer non-solvent having a boiling point of 348°–376°F.) with agitation. The solution is sprayed into a lubricated chromium-plated mold having a depth of 25 mils until the mold is full. The mold is then allowed to dry at room temperature (approximately 74°F.). The resulting film is approximately 6 mils thick, has a reflectance of 97% for visible light and greater than 90% for ultraviolet light and has therein a plurality of microcells. Upon aging, the retains its high reflectivity.

EXAMPLE 7 the same procedure is followed as set forth in Example 6 except that 25 grams of Isopar H instead of 50 grams thereof is used. The film formed containg closed microcells and upon aging retained the same high reflectivity as the film in Example 6.

EXAMPLE 8

The same procedure is followed using polyfluorochloroethylene. The resulting film is approximately 6 mils thick, has a plurality of small cells, and exhibits a reflectance of greater than 90% in the above mentioned light ranges. This level of reflectance is maintained even after two weeks of use.

EXAMPLE 9

A plate of aluminum suitable for mounting at form 4 in FIG. 1 is coated with a conventional clear acrylic lacquer. Polyvinylidene fluoride (Kynar 500) is then powdered to a grain size of approximately 5 microns. This powder is then dry sprayed against the still wet lacquer until the surface of the plate is entirely covered and no more powder will adhere to it. The resulting coating is approximately 5 mils thick, exhibits good aging, and has a reflectance greater than 90% in the above mentioned light rangers.

EXAMPLE 10

The same procedure is followed as in Example 8 except that the substrate is a light integrating sphere 2 as shown in FIG. 1 and the inner wall or surface 3 of the sphere is coated with lacquer. The resulting polyvinylidene fluoride coating 6 applied to the lacquered surface 3 is about 4 mils thick, exhibits excellent aging and has a reflectance of greater than 90% when used with light in the 2400 to 8000 Angstrom region.

EXAMPLE 11

The same procedure is followed as set forth in Example 6 except that instead of molding the film, the film is sprayed onto an aluminum plate suitable for mounting at 4 in FIG. 1. The resulting coating is a film of about 6 mils having therein a plurality of tiny cells. This coating exhibits excellent aging qualities and reflects greater than 95% of incident light across the 2400 to 8000 Angstrom wave length range.

EXAMPLE 12

The same procedure is followed as in Example 10 except the substrate used is a light integrating sphere 2 as shown in FIG. 1. The resulting 6 on inner wall 3 is about 5 mils thick and exhibits substantially the same characteristics as the coating in Example 10.

EXAMPLE 13

The same procedure is followed as in Example 11 except the powder used is a mixture of polyvinyl fluoride and polyflurochloroethylene. The resulting coating 6 is approximately 8 mils thick and exhibits a reflectance of greater than 95% in the 2400 to 8000 Angstrom region.

EXAMPLE 14

Fifty grams of polyvinylidene fluoride (trade-name: Kynar 500) are prewetted with a mixture of 50 grams Isopar H and 1.5 grams of Sanchan Yellow 10-G pigment (hansa yellow pigment produced by National Analine Div. of Allied Chem. Corp.). To the prewetted polyvinylidene fluoride is added 550 grams of hot adetone (100°F.) and the polyvinylidene fluoride dissolved therein. The solution is sprayed into a lubricated chromium plated mold having a depth of 25 mils until the mold is full. The mold solution is then allowed to dry at room temperature (approximately 74°F.). The resulting film is approximately 6 mils thick, is bright yellow, and reflects more than 90% incident light of wavelengths between 540 millimicrons and 700 millimicrons. The film exhibits good durability upon aging and because of its reflectance characteristics, it may be used as a color standard for hansa yellow.

EXAMPLE 15

A mixture of 550 gms. acetone, 50 gms. polyvinylidene fluoride (tradename: Kynar 500), and 50 gms. Isopar H is thoroughly mixed and heated until the polyvinylidene fluoride is dissolved in the acetone. To this mixture is then added 7 gms. of a coloring paste. The coloring paste used is made by first forming mixture of 650 gms. acetone, 50 gms. polyvinylidene fluoride and 50 gms. quinacridone red (RM 3445). This mixture is then thoroughy ground for 30 minutes to a paste in a jiff Mill whereinafter 7 grams of this ground paste are added to the acetone-kynar-Isopar H mixture as above set forth. This total mixture now containing 7 gms. of a coloring paste is drawn as a film by a standard drawbar technique. The resulting film upon removal of acetone and Isopar H is a bright red with high reflectance.

EXAMPLE 16

The following comparative analysis points out the ability of the coatings of this invention to reflect light and thus prevent undue heating of the inside of a container when placed in the sun or other source of heat and light. Because of this characteristic, the coatings of this invention have found particular utility as paints for outside surfaces of tanks containing volatile and combustible gases and liquids, such as oil, gasoline, natural gas, and the like.

In the following analysis, a film of polyvinylidene fluoride was compared against a film of commercially available vinyl white paint having a ratio of $TiO_2$ to binder of 1:1, and against a non-pigmented cellular film of non-fluoride containing polymer. In each instance the films were 4 mils thick. The comparison was conducted as follows: (1) A one quart metal can was painted with the commercially available vinyl white paint as described above (trade symbol UL 8134) until the coating thereon was 4 mils thick. (2) A second one quart metal can was then coated with a non-fluorinate vinyl cellular film. This was accomplished as follows: (all parts are by weight unless otherwise specified): 55.5 parts of VYHH, a copolymer of 87 parts vinyl chloride per 13 parts vinylacetate, were mixed with 37.0 parts VMCH, a copolymer of 86 parts vinyl chloride and 13 parts vinyl acetate, per 1 part maleic acid. This copolymer mixture was then dissolved in a solvent consisting of 166.5 parts teluene and 277 parts methylethyl ketone. To this solution was then added a nonsolvent consisting of 157.1 parts V.M. & P. naptha. Also added was 2.1 parts poly 2-ethylhemylacrylate in order to insure that the surface of the final film was smooth. In addition there was also added 33.3 parts Syloid (a finely divided silica) and 3.7 parts Cabosil (a pyrogenic silica), both of which are light transparent and used to insure that solvent release will be effective. This complete mixture was then thoroughly stirred and brushed on the second 3 quart can. After the solvent and non-solvent evaporated there was formed a film of approximately 4 mils in thickness having a plurality of discrete cells therein which rendered the film very white and opaque. (3) A one quart metal can was then coated with a film of this invention. This was accomplished as follows: 25 grams of polyvinylidene fluoride (tradename Kynar 500 special) where prewetted with 25 gms. Isopar H and dissolved in 100 gms. of acetone by heating to 120°F. with agitation. This mixture was then sprayed on the 1 quart can after the can had previously been preprimed with a thin clear coat of 15%

VMCH (as hereinbefore defined) solution wherein the solvents were toluene and methylisobutylketone in a 1:1 ratio. This preprime coat is transparent to light and is applied solely for the purpose of providing a surface to which the polyvinylidene film will adhere. On top of the first coat of polyvinylidene film was added another coat of polyvinylidene film which was formed similarly to the first coat mixture except that 55 gms. of polyvinylidene fluoride and 55 gms. of Isopar H were used. Both films were very white, opaque films having discrete cells therein. The purpose of two coats of different compositions was to bring the total thickness of the polyvinylidene films up to 4 mils as well as to provide a more adherent undercoat while providing a smoother top-coat.

Each of the three coated cans was then placed in the direct beam of a Westinghouse 150 watt projector spotlight located 6 inches from the can. The following results were recorded:

TABLE I

| Time (Min) | Temp. (° F) of Inside of can No. 1 (coated with white commercial paint) | Temp. (° F) of Inside of can No. 3 (coated with film of polyvinylidene fluoride) | $\Delta\gamma$ (° F.) |
|---|---|---|---|
| 0 | 75.0 | 75.0 | 0 |
| 2 | 78.0 | 75.0 | 3.0 |
| 4 | 82.25 | 76.75 | 5.5 |
| 6 | 87.25 | 79.00 | 8.25 |
| 8 | 90.00 | 80.50 | 9.50 |
| 10 | 92.50 | 82.0 | 10.50 |
| 12 | 94.25 | 83.0 | 11.25 |
| 14 | 95.00 | 83.75 | 11.25 |
| 16 | 95.75 | 84.50 | 11.25 |
| 20 | 96.75 | 85.25 | 11.50 |
| 22 | 97.25 | 85.75 | 11.50 |
| 24 | 98.00 | 86.00 | 12.00 |
| 26 | 98.25 | 86.25 | 12.00 |
| 28 | 98.50 | 86.75 | 11.75 |
| 30 | 98.75 | 86.75 | 12.00 |

As is readily seen from an analysis of the results recorded in Table I, the films of this invention represent a marked improvement over a commercially available pigmented paint used for the same purpose.

TABLE II

| Time (Min) | Temp. (° F) of inside of can No. 2 (coated with non-fluorinated vinyl polymer) | Temp. (° F) of inside of can No. 3 (coated with film of polyvinylidene fluoride) | $\Delta\gamma$ (° F) |
|---|---|---|---|
| 0 | 72.5 | 72.5 | 0 |
| 2 | 73.75 | 73.50 | .25 |
| 4 | 77.00 | 75.25 | 1.75 |
| 6 | 80.00 | 77.50 | 2.50 |
| 8 | 82.25 | 79.50 | 2.75 |
| 10 | 84.50 | 81.00 | 3.50 |
| 12 | 85.75 | 82.25 | 3.50 |
| 14 | 86.75 | 83.25 | 3.50 |
| 16 | 87.25 | 84.00 | 3.25 |
| 18 | 88.00 | 84.25 | 3.75 |
| 20 | 88.25 | 84.75 | 3.50 |
| 22 | 88.50 | 85.00 | 3.50 |
| 24 | 88.75 | 85.00 | 3.75 |
| 26 | 89.00 | 85.50 | 3.75 |
| 28 | 89.25 | 85.50 | 3.75 |
| 30 | 89.50 | 85.75 | 3.75 |

An analysis of Table II clearly discloses the superiority of films formed from the materials of this invention when compared with a non-fluorinated material used for the same purpose.

Once given the above disclosure many other features, modifications and embodiments of this invention will become apparent to the skilled artisan. For this reason these features, modifications and embodiments are included in this invention the scope of which is defined by the following claims.

I claim:

1. In the method of comparing the light reflectance of a sample against a standard, the improvement comprising using as said standard a material which is comprised of at least one fluorinated aliphatic long chain addition polymer having at least one monomer wherein at least one fluorine atom is attached to a chain carbon, atom, said standard being light stable and of sufficient thickness to reflect more than 90 percent of incident light having a wave length of from 2400 to 8000 Angstrom units.

2. An improvement according to claim 1 wherein said material is white and non-pigmented and said polymer consists essentially of polyvinylidene fluoride.

3. In the method of comparing the color of a sample against a standard, the improvement comprising using as said standard a standard a material which is comprised of (a) at least one fluorinated aliphatic long chain addition polymer having at least one monomer wherein at least one fluorine atom is attached to a chain carbon atom and (b) a coloring pigment, said standard being of sufficient thickness to reflect more than 90 percent of incident light having a wave length transparent to said pigment, said wave length being between 2400 and 8000 Angstrom units.

4. An improvement according to claim 3 wherein said material consists essentially of a film of said polymer having therein a plurality of discrete cells at least some of which contain particles of said pigment.

5. An improvement according to claim 4 wherein said polymer is polyvinylidene fluoride.

6. in an apparatus for comparing the light reflectance of a substance against a standard which includes a reflectance standard the improvement comprising a reflectance standard consisting essentially of at least one fluorinated aliphatic long chain addition polymer having at least one monomer wherein at least one fluorine atom is attached to a chain carbon atom, said standard being light stable and of sufficient thickness to reflect more than 90 percent of incident light having a wave length of from 2400 to 8000 Angstrom units.

7. An improvement according to claim 6 wherein said standard is white, and non-pigmented and said polymer is polyvinylidene fluoride.

8. In an apparatus for comparing the color of a substance against a standard which includes a color standard, the improvement comprising a color standard consisting essentially of (a) at least one fluorinated aliphatic long chain addition polymer having at least one monomer wherein at least one fluorine atom is attached to a chain carbon atom and (b) a coloring pigment, said standard being of sufficient thickness to reflect more than 90 percent of incident light having a wave length transparent to said pigment, said wave length being 2400 and 8000 angstrom units.

9. An improvement according to claim 8 wherein said standard consists essentially of a film of polyvinylidene fluoride having therein a plurality of discrete cells at least some of which contain particles of said coloring pigment.

10. An improvement according to claim 8 wherein said standard consists essentially of a film of polyvinylidene fluoxide having therein a plurality of discrete cells, said film containing particles of said coloring pigment.

* * * * *